(12) United States Patent
Butler et al.

(10) Patent No.: US 11,191,574 B2
(45) Date of Patent: Dec. 7, 2021

(54) SET SCREW REDUCER FOR MODULAR REDUCTION SCREWS

(71) Applicant: Warsaw Orthopedic, Inc., Warsaw, IN (US)

(72) Inventors: Brian A. Butler, Atoka, TN (US); William A. Rezach, Covington, TN (US); Molly K. Rice, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 3 days.

(21) Appl. No.: 16/820,804

(22) Filed: Mar. 17, 2020

(65) Prior Publication Data

US 2021/0290278 A1 Sep. 23, 2021

(51) Int. Cl.
*A61B 17/70* (2006.01)
*A61B 17/86* (2006.01)
*A61B 17/88* (2006.01)
*A61B 17/56* (2006.01)

(52) U.S. Cl.
CPC ...... *A61B 17/7082* (2013.01); *A61B 17/7032* (2013.01); *A61B 17/8685* (2013.01); *A61B 2017/564* (2013.01)

(58) Field of Classification Search
CPC . A61B 17/7035; A61B 17/7082; A61B 17/86; A61B 17/8886; A61B 17/7091; A61B 17/7086; A61B 17/7037; A61B 17/7032; A61B 17/7049; A61B 17/7076; A61B 17/8875; A61B 17/8685; A61B 17/00234; A61B 17/702; A61B 17/844; A61B 17/864; A61B 17/8645; A61B 17/888; A61B 17/8894; A61B 17/8877; A61B 2017/564; A61B 34/10; A61B 34/3743; A61B 2034/2051; A61B 2034/2055; A61B 90/39; A61B 2090/037; A61B 2090/3966; A61B 2090/3762
USPC ....................................... 606/246–279, 86 B
See application file for complete search history.

(56) References Cited

U.S. PATENT DOCUMENTS

| | | | |
|---|---|---|---|
| 6,251,112 B1 | 6/2001 | Jackson | |
| 7,771,430 B2 | 8/2010 | Jones et al. | |
| 7,799,031 B2 | 9/2010 | Miller et al. | |
| 8,172,847 B2 | 5/2012 | Dziedzic et al. | |
| 8,231,635 B2 | 7/2012 | Sharifi-Mehr et al. | |
| 8,317,796 B2 | 11/2012 | Stihl et al. | |
| 8,403,933 B2 | 3/2013 | Rutledge | |
| 8,834,474 B2 | 9/2014 | Jones et al. | |
| 8,998,921 B2 | 4/2015 | Sharifi-Mehr et al. | |
| 9,050,148 B2 | 6/2015 | Jackson | |
| 9,265,533 B2 | 2/2016 | Nelson et al. | |

(Continued)

*Primary Examiner* — Pedro Philogene
(74) *Attorney, Agent, or Firm* — Fox Rothschild LLP

(57) ABSTRACT

Systems, instruments, and methods for advancing a set screw in an object. The methods comprise: disposing a shank tip of a set screw reducer in a socket of the set screw; causing a sleeve integrated with the set screw reducer to slidingly engage a shank of the set screw reducer and move in a direction towards the shank tip; transferring torque from the set screw reducer to the set screw such that the set screw is advanced in a threaded hole of the object; and using the sleeve of the set screw reducer to substantially prevent splaying of at least one sidewall of the object while the torque is being transferred from the set screw reducer to the set screw.

21 Claims, 11 Drawing Sheets

(56) References Cited

U.S. PATENT DOCUMENTS

| | | |
|---|---|---|
| 9,295,501 B2 | 3/2016 | Hammer |
| 9,402,662 B2 | 8/2016 | Mahar |
| 9,517,099 B2 | 12/2016 | Bess et al. |
| 9,636,151 B2 | 5/2017 | Jackson |
| 9,649,139 B2 | 5/2017 | Sharifi-Mehr et al. |
| 9,681,961 B2 | 6/2017 | Prevost et al. |
| 9,707,019 B2 | 7/2017 | Miller et al. |
| 9,750,548 B2 | 9/2017 | George |
| 9,901,378 B2 | 2/2018 | Dauster et al. |
| 9,907,577 B2 | 3/2018 | Jackson |
| 9,924,982 B2 | 3/2018 | Jackson |
| 9,980,758 B2 | 5/2018 | Abidin |
| 9,987,066 B2 | 6/2018 | Stad et al. |
| 10,058,355 B2 | 8/2018 | Beyer |
| 10,154,862 B2 | 12/2018 | Miller et al. |
| 10,159,579 B1 | 12/2018 | Reitblat et al. |
| 10,258,391 B2 | 4/2019 | Jackson |
| 10,299,839 B2 | 5/2019 | Sicvol et al. |
| 10,363,068 B2 | 7/2019 | Abell et al. |
| 10,405,897 B2 * | 9/2019 | Beretta ............... A61B 17/7091 |
| 10,448,978 B2 | 10/2019 | Wall et al. |
| 10,463,404 B2 | 11/2019 | Wall et al. |
| 10,512,491 B2 | 12/2019 | Bazille |
| 10,575,881 B2 | 3/2020 | Krier et al. |
| 2004/0158247 A1 | 8/2004 | Sitiso et al. |
| 2006/0293680 A1 | 12/2006 | Jackson |
| 2009/0105718 A1 | 4/2009 | Zhang et al. |
| 2011/0184469 A1 * | 7/2011 | Ballard ............... A61B 17/7086 606/279 |
| 2015/0105831 A1 | 4/2015 | Yim et al. |
| 2015/0250520 A1 * | 9/2015 | Rezach ............... A61B 17/8891 606/104 |
| 2017/0079696 A1 | 3/2017 | Walker et al. |
| 2017/0231670 A1 | 8/2017 | Sharifi-Mehr et al. |
| 2017/0325856 A1 | 11/2017 | George |
| 2017/0348029 A1 | 12/2017 | Asaad |
| 2018/0036046 A1 | 2/2018 | Yim et al. |
| 2018/0110544 A1 | 4/2018 | Simpson et al. |
| 2018/0168702 A1 | 6/2018 | Jackson |
| 2018/0185072 A1 | 7/2018 | Rubin et al. |
| 2018/0214190 A1 | 8/2018 | Erramilli et al. |
| 2018/0250039 A1 | 9/2018 | Jackson |
| 2018/0256234 A1 | 9/2018 | Stad et al. |
| 2018/0353225 A1 | 12/2018 | Asaad et al. |
| 2018/0368902 A1 * | 12/2018 | Milor ................... B25B 15/005 |
| 2019/0117267 A1 | 4/2019 | Sicvol et al. |
| 2019/0209217 A1 | 7/2019 | Jackson |
| 2019/0209218 A1 | 7/2019 | Jackson |
| 2019/0216506 A1 | 7/2019 | Sicvol et al. |
| 2019/0307493 A1 | 10/2019 | Jackson |
| 2019/0357948 A1 | 11/2019 | Wall et al. |
| 2019/0374263 A1 | 12/2019 | Wall et al. |

* cited by examiner

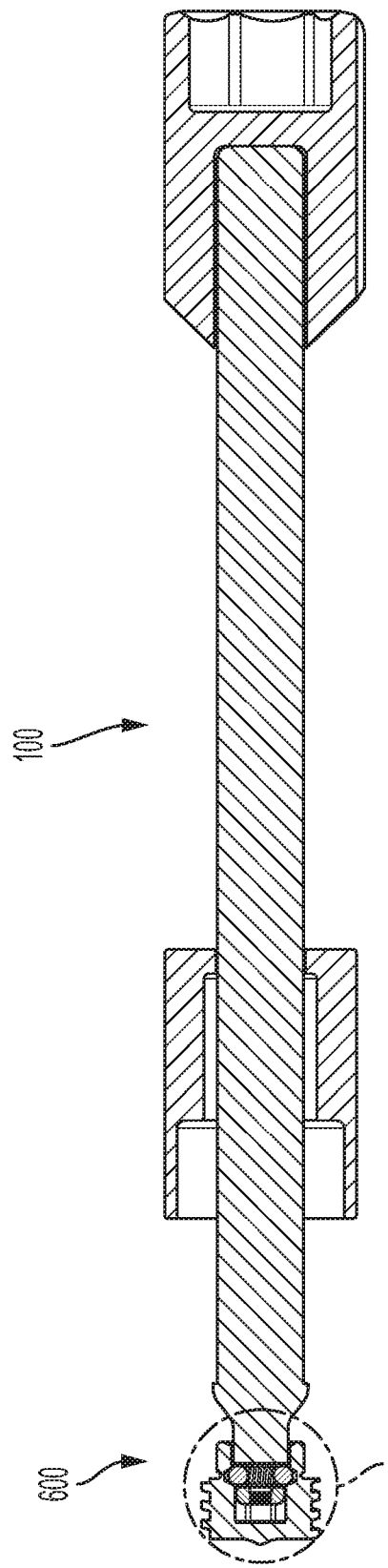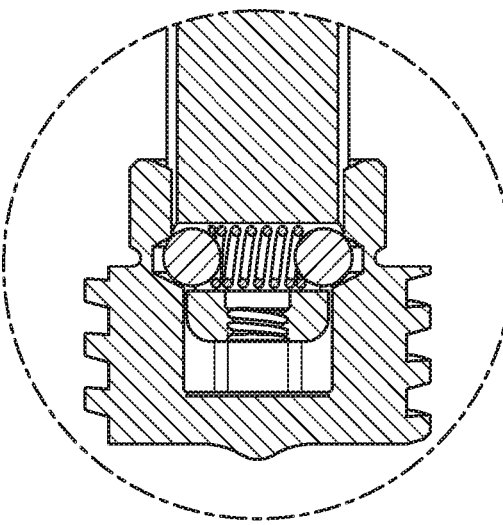
FIG. 8A
FIG. 8B

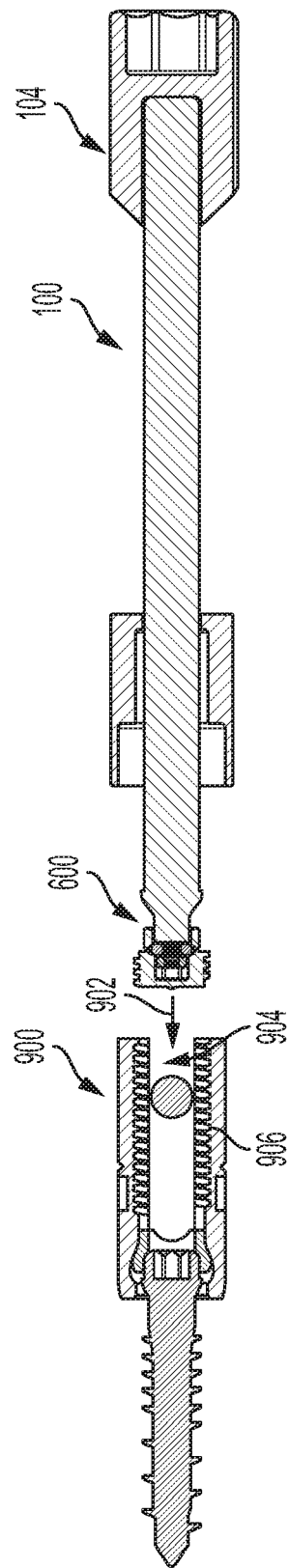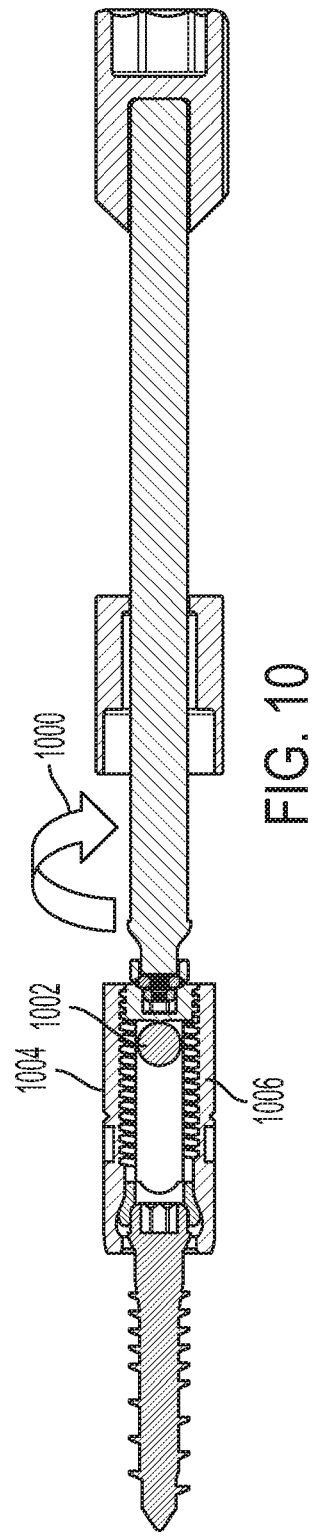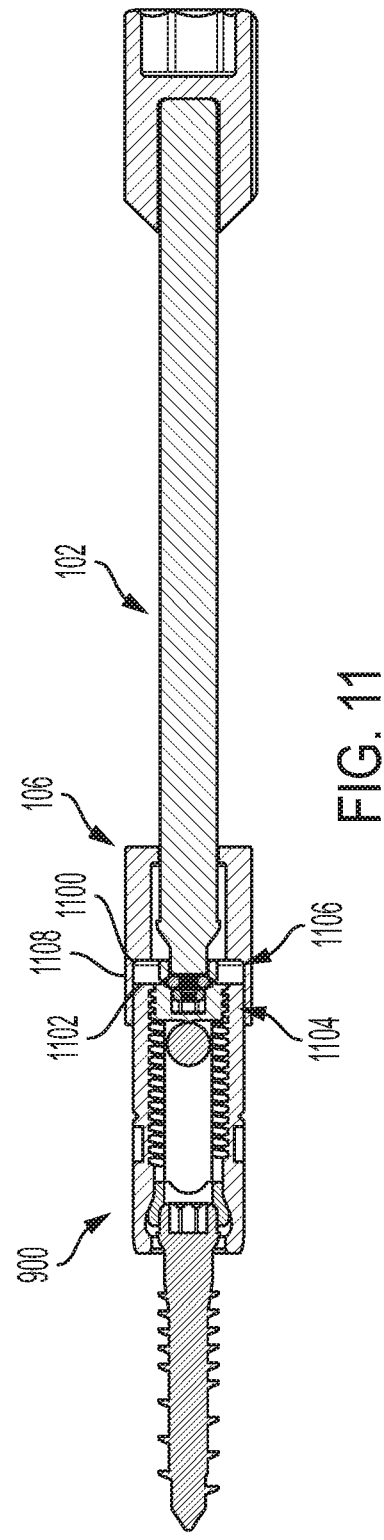

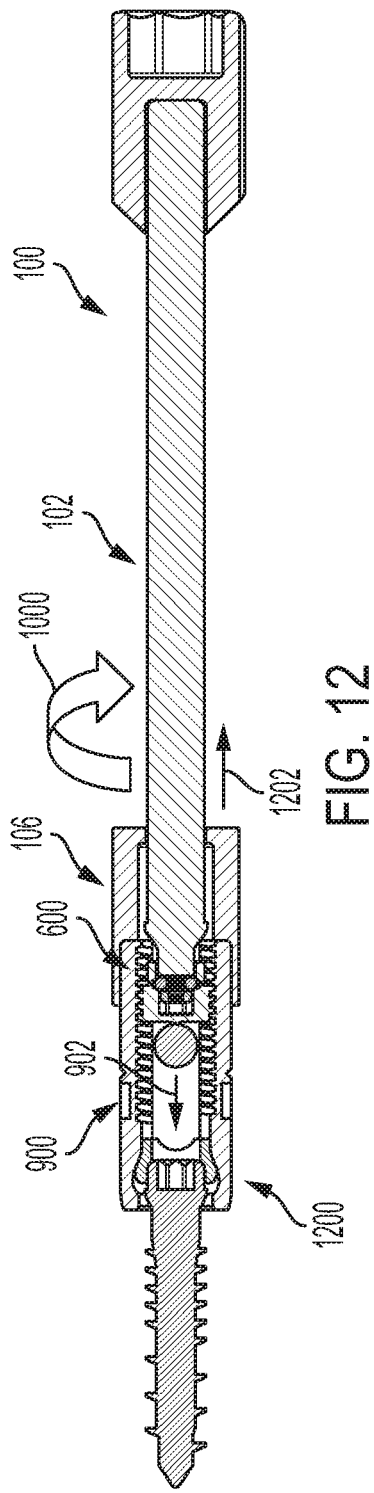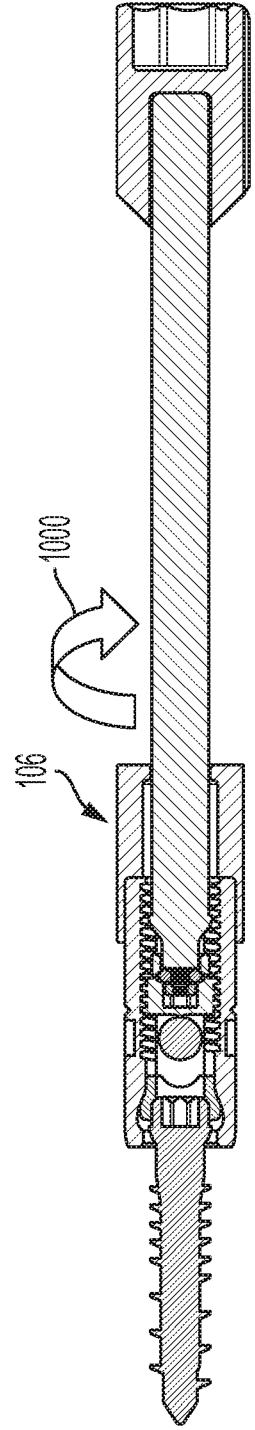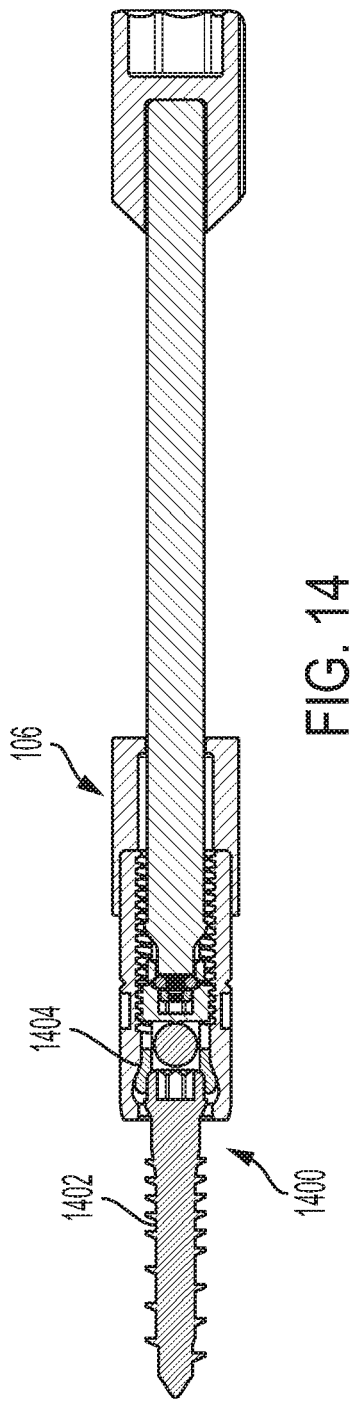

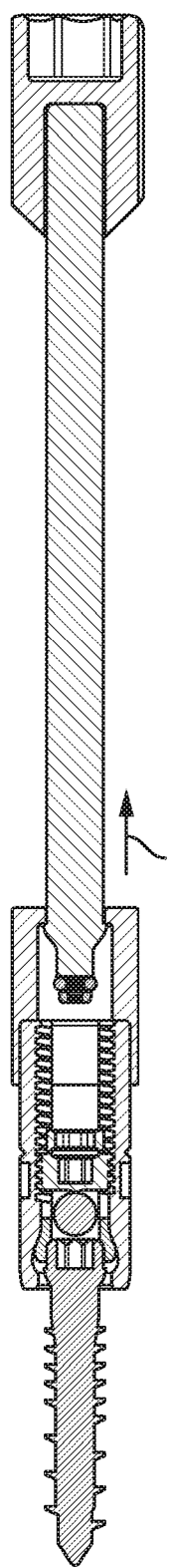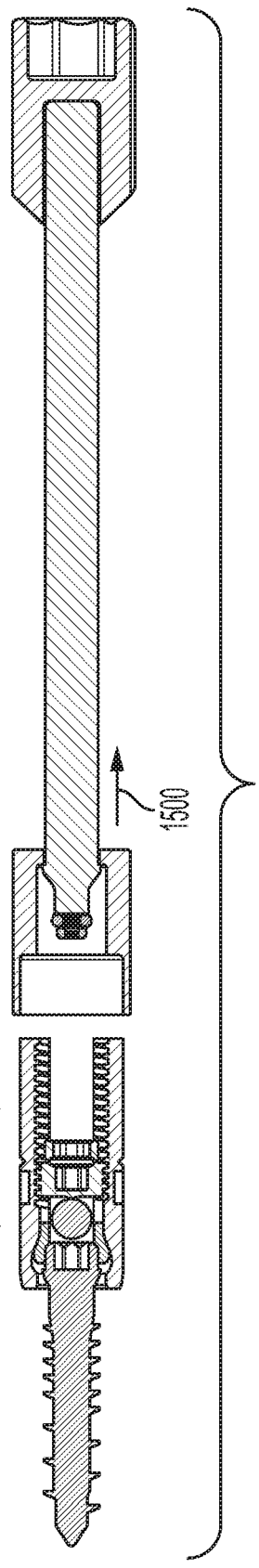

SET SCREW REDUCER FOR MODULAR REDUCTION SCREWS

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation, and exercise can be effective, however, may fail to relieve the symptoms associated with these disorders. Surgical treatment of these spinal disorders includes correction, fusion, fixation, discectomy, laminectomy, and/or implantable prosthetics. As part of these surgical treatments, spinal constructs, which include implants such as bone fasteners, connectors, plates, and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attachment to two or more vertebral members. This disclosure describes improvements over these prior technologies.

SUMMARY

The present disclosure relates to implementing systems and methods for advancing a set screw in an object. The methods comprise: sliding a sleeve of a set screw reducer along an elongate length of a shank of the set screw reducer in a direction away from the shank's tip until the sleeve is in a position which decreases, reduces or eliminates the sleeve's interference with a coupling between the set screw reducer (or driver) and the set screw; disposing the shank's tip in a socket of the set screw; causing the sleeve to slidingly engage the shank of the set screw reducer and move in a direction towards the shank tip; transferring torque from the set screw reducer to the set screw such that the set screw is advanced in a threaded hole of the object (e.g., in response to a rotational force being applied to a handle of the set screw reducer); and using the sleeve of the set screw reducer to substantially prevent splaying of at least one sidewall of the object while the torque is being transferred from the set screw reducer to the set screw. The term "substantially" as used herein means the object's sidewall remains disposed within the sleeve and/or remains in contact with a sidewall of the sleeve.

In some scenarios, the sleeve, as part of splaying prevention, resists an outward bending of the at least one sidewall of the object throughout the advancement of the set screw in the object. A free end of the at least one sidewall of the object may be continuously disposed within a recess formed in the sleeve, while the set screw reducer is being used to advance the set screw in the object. The free end of the at least one sidewall of the object causes the sleeve to move along an elongate length of the shank in a direction away from the shank tip while the set screw is being advanced in the object.

In those or other scenarios, the methods may further comprise: receiving an end of an external instrument or tool in a socket formed in a handle of the set screw reducer; and using the external instrument or tool to cause rotation of the handle.

Additionally or alternatively, the methods comprise establishing a frictional engagement between the shank tip and the set screw. The frictional engagement may be established by resiliently biasing at least one engagement part of the set screw reducer into a detent or a groove formed in a sidewall of the socket of the set screw. The engagement part may include, but is not limited to, a ball bearing that is resiliently biased by a resilient member in a direction out and away from the shank tip.

The disclosure also relates to a surgical instrument (e.g., a set screw reducer or driver). The surgical instrument comprises: a shank having a shank tip sized and shaped to fit in a socket of a set screw; and a sleeve disposed on the shank such that the sleeve slidingly engages the shank to move at least in a first direction towards the shank tip. Torque is transferable from the shank to the set screw such that the set screw is advanced in a threaded hole of an object (e.g., in response to a rotational force being applied to a handle of the surgical instrument). The sleeve prevents splaying of at least one sidewall of the object while the torque is being transferred from the shank to the set screw.

The sleeve is also able to slide along an elongate length of the shank in a direction away from the shank tip until the sleeve is in a positon which substantially eliminates the sleeve's interference with a coupling between the surgical instrument and the set screw. The term "substantially" as used here means the sleeve is not blocking the coupling. As part of the splaying prevention, the sleeve resists an outward bending of the at least one sidewall of the object throughout the advancement of the set screw in the object. In this regard, it should be understood that a free end of the at least one sidewall of the object is continuously disposed within a recess formed in the sleeve, while the surgical instrument is being used to advance the set screw in the object. The free end of the at least one sidewall of the object causes the sleeve to move along an elongate length of the shank in a direction away from the shank tip while the set screw is being advanced in the object.

In some scenarios, the surgical instrument also comprises a handle having a socket to receive an end of an external instrument or tool that facilitates rotation of the handle during advancement of the set screw in the object. Additionally or alternatively, the surgical instrument comprises a frictional retention structure that establishes a frictional engagement between the shank tip and the set screw. The frictional engagement may be established by resiliently biasing at least one engagement part of the frictional retention structure into a detent or a groove formed in a sidewall of the socket of the set screw. The engagement part may include, but is not limited to, a ball bearing that is resiliently biased by a resilient member in a direction out and away from the shank tip.

The foregoing and other objects, features and advantages of the invention will be apparent from the following more particular descriptions of exemplary embodiments of the invention as illustrated in the accompanying drawings wherein like reference numbers generally represent like parts of the disclosure.

BRIEF DESCRIPTION OF DRAWINGS

The following drawings are illustrative of particular embodiments of the present disclosure and therefore do not limit the scope of the present disclosure. The drawings are not to scale and are intended for use in conjunction with the explanations in the following detailed description.

FIGS. 8A-8B (collectively referred to herein as "FIG. 8") provide illustrations showing the set screw of FIGS. 6-7 coupled to the set screw reducer of FIGS. 1-4.

FIGS. 9-16 provide illustrations that are useful for understanding how the set screw reducer operates.

DETAILED DESCRIPTION

Figure 1:
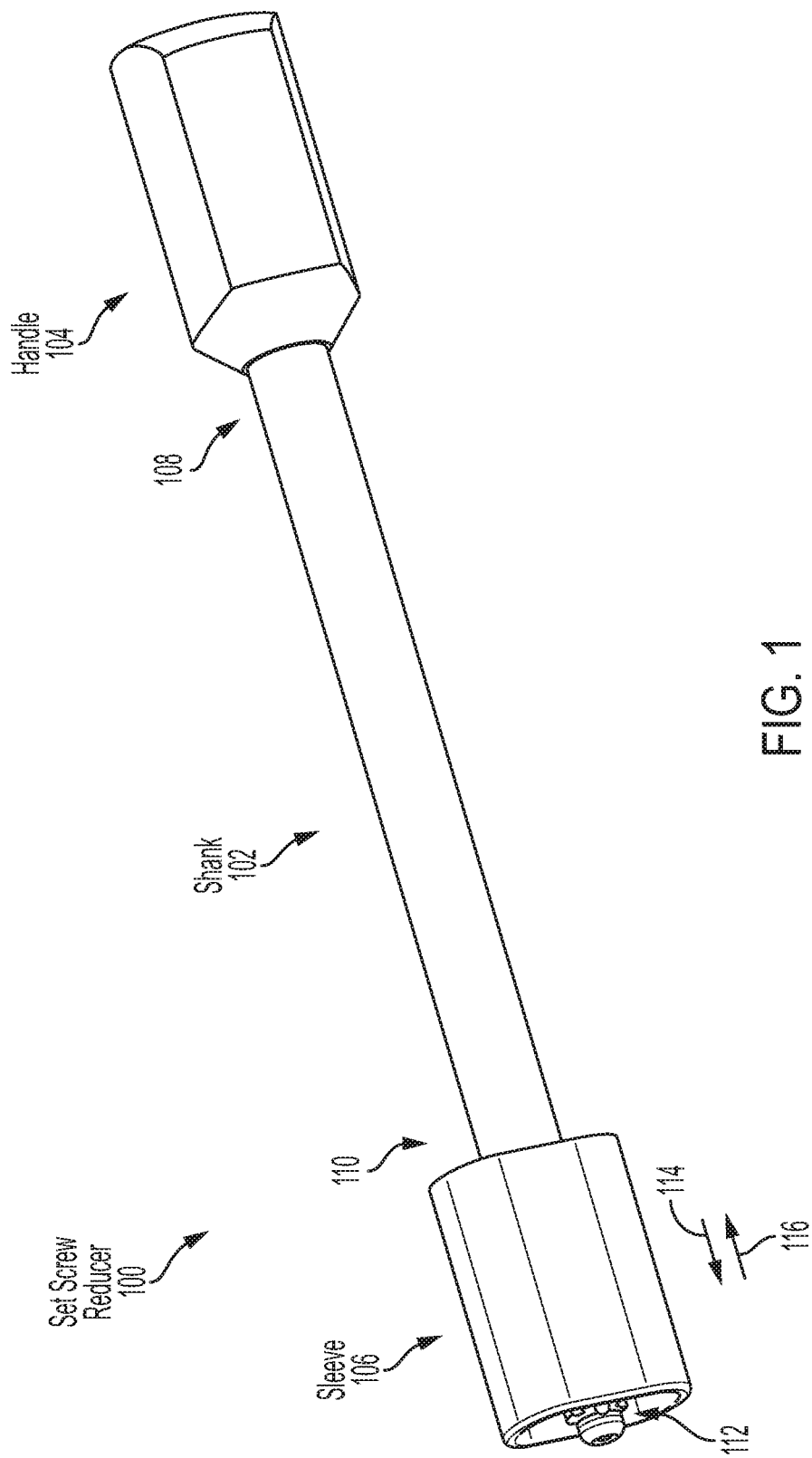
FIG. 1 is a perspective view of an illustrative set screw reducer.

The following discussion omits or only briefly describes certain conventional features related to surgical systems for treating the spine, which are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally, for example, to medical devices and methods for treating musculoskeletal disorders, and more particularly, to surgical systems and methods for treating the spine. Embodiments of the devices, methods, and systems are described below with reference to the Figures.

Figure 2:
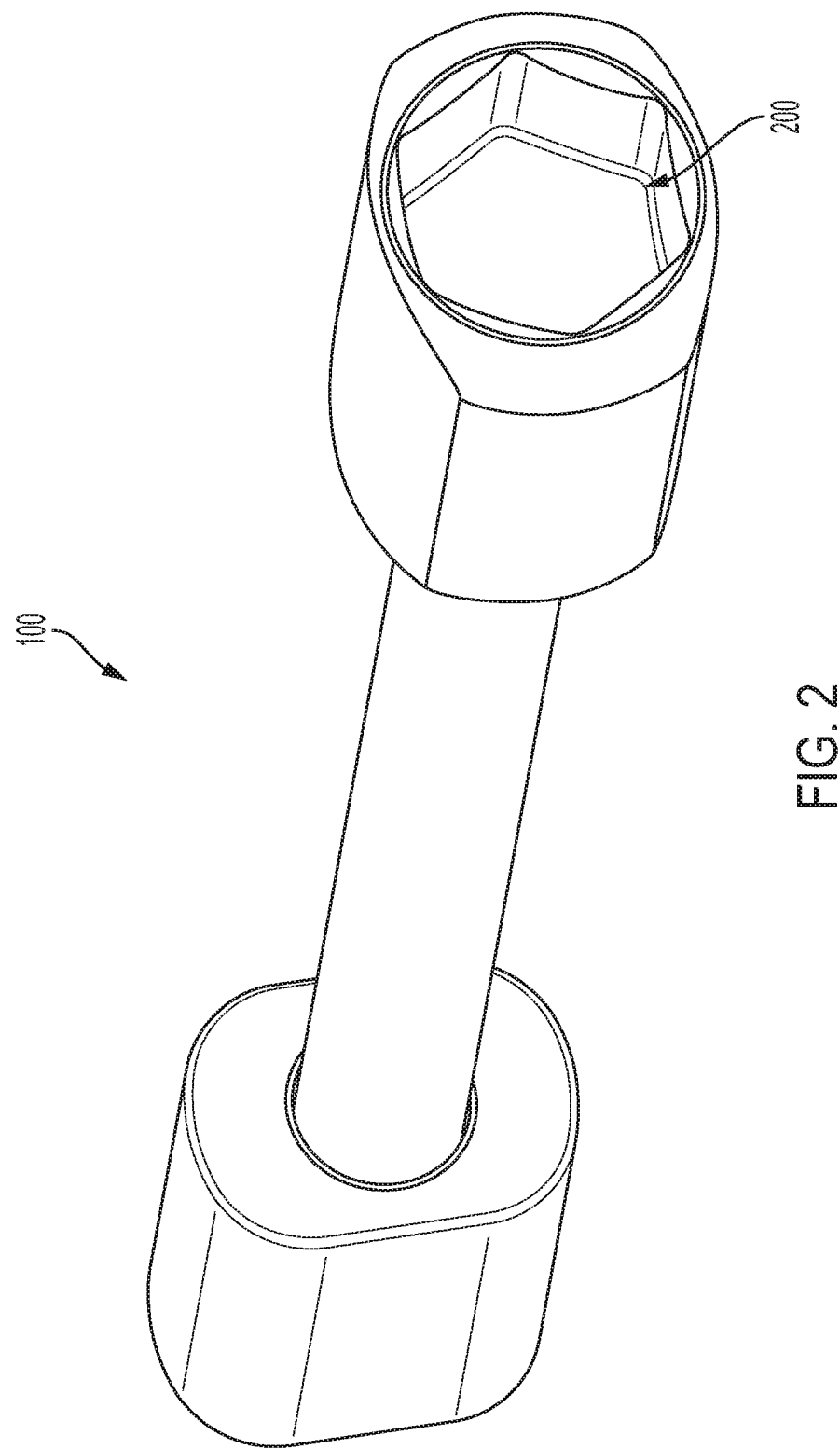
FIG. 2 is another perspective view of the illustrative set screw reducer shown in FIG. 1.
Figure 3:
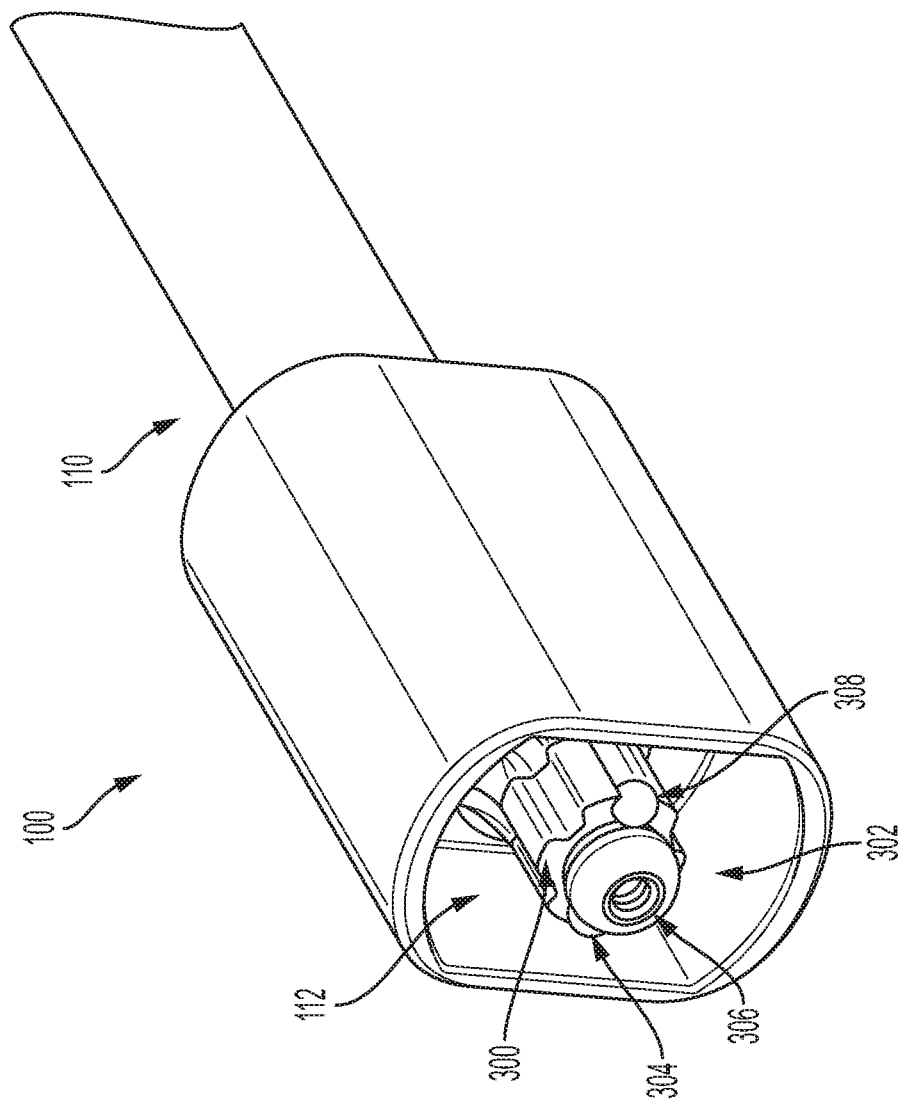
FIG. 3 is a perspective view of a distal end of the set screw reducer shown in FIGS. 1-2.
Figure 4:
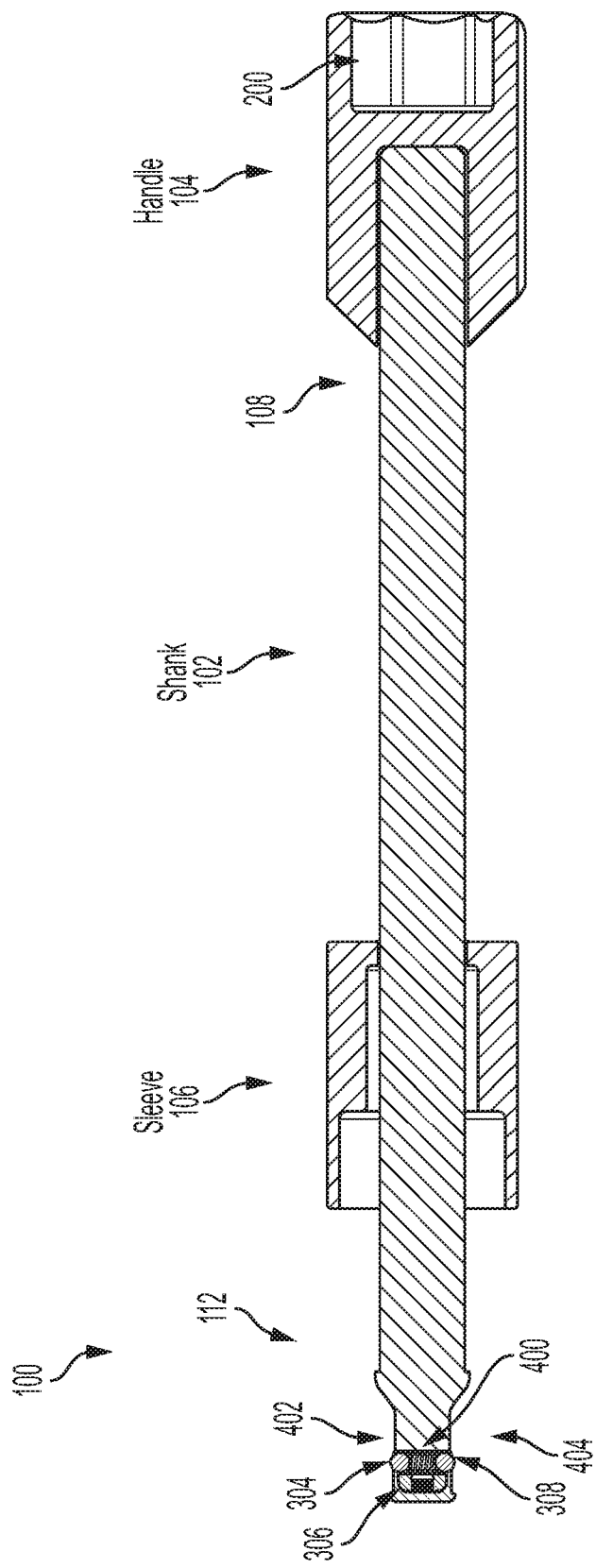
FIG. 4 is a cross-sectional view of the set screw reducer.

FIGS. 1-3 provide perspective views of a set screw reducer 100. A cross-sectional view of the set screw reducer is provided in FIG. 4. As shown in FIGS. 1-4, the set screw reducer 100 comprises a shank 102 and a handle 104. The handle 104 resides at a proximal end 108 of the shank 102. The shank 102 and handle 104 may be integrally formed as one part (not shown), or alternatively be coupled to each other via a coupling means as shown in FIG. 4. The coupling means can include, but is not limited to, a weld, adhesive, and/or threads. The shank 102 and handle 104 are formed of stainless steel, titanium or other alloy which is resistant to corrosion. The handle 104 has a size and shape that allows an individual to easily grip and turn the same without discomfort. The handle 104 transfers torque from the individual to the shank 102.

Notably, the handle 104 has a socket 200 formed therein as shown in FIG. 2 and FIG. 4. The socket 200 is sized and shaped to receive an end of an external instrument or tool (e.g., a power attachment, or a manual wrench) that can facilitate the rotation of the shank 102. The external instrument or tool may optionally be employed when it becomes difficult for the individual to apply torque to the set screw reducer 100 when driving a screw (e.g., such as screw 600 shown in FIGS. 6-7) into an object (e.g., a bone, an implant or a receiver during a medical procedure).

Figure 5:
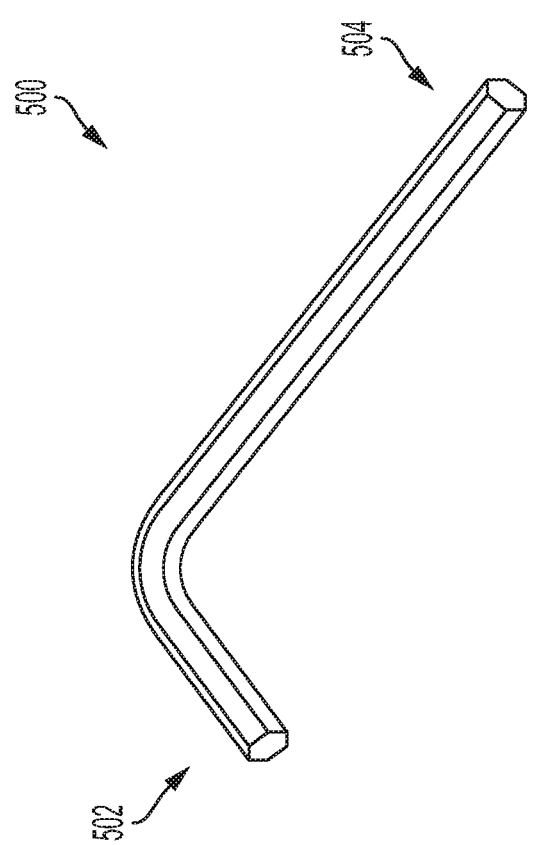
FIG. 5 is an illustration of an illustrative external instrument or tool that can be used with the set screw reducer of FIGS. 1-4.

The external instrument or tool can include, but is not limited to, a power attachment with a hex bit, or a manual Allen wrench. Power attachments and Allen wrenches are well known in the art, and therefore will not be described here. For example, an illustrative Allen wrench is shown in FIG. 5. In the Allen wrench scenario, the socket 200 has a hexagonal shape and the Allen wrench 500 has a hexagonal head at each end 502, 504 which can be inserted into the hexagonal shaped socket 200 of the set screw reducer 100. A torque may be applied to the set screw reducer 100 by the Allen wrench 500, whereby the set screw reducer is caused to rotate. The set screw reducer 100 transfers the torque to the set screw (e.g., set screw 600 of FIGS. 6-7), whereby the set screw is caused to rotate such that the set screw is advanced into or driven out of an object (e.g., a bone, an implant, or a receiver during a medical procedure). The present solution is not limited to the particulars of this example.

Figure 7:
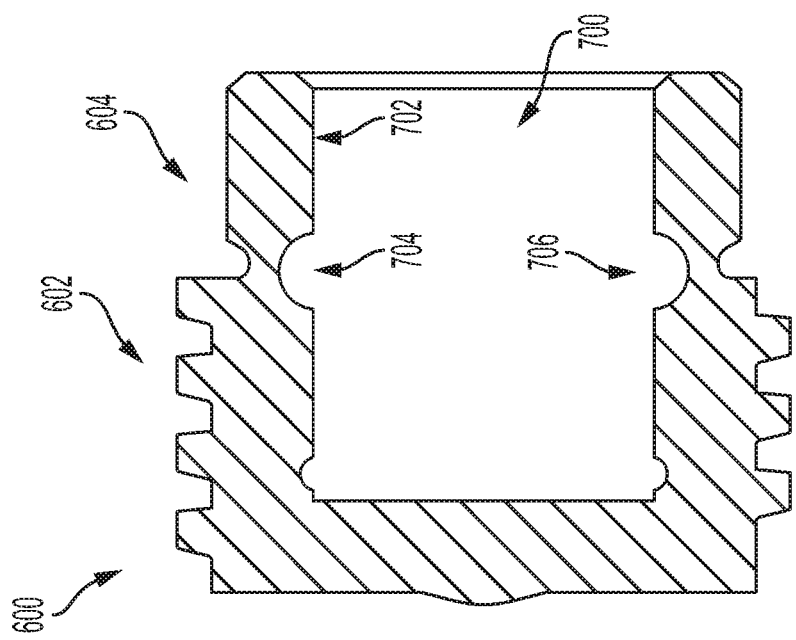
FIG. 7 is a cross-sectional view of the illustrative set screw shown in FIG. 6.
Figure 6:
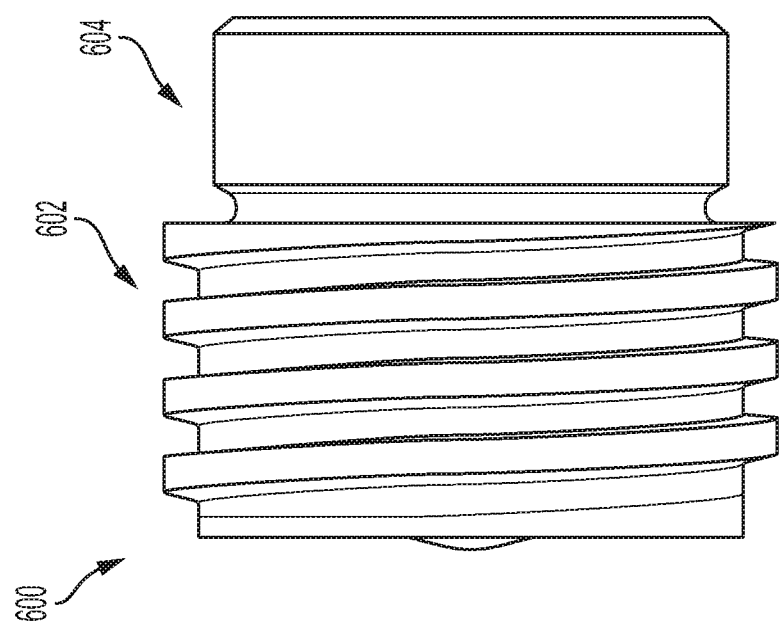
FIG. 6 is a side view of an illustrative set screw that may be used with the set screw reducer of FIGS. 1-4.

Set screws are well known in the art, and therefore will not be described herein. Any known or to be known set screw can be used herein without limitation. Still, an illustrative set screw 600 is shown in FIGS. 6-7. The features of set screw 600 will become apparent as the discussion progresses.

The set screws that are used with the set screw reducer 100 may be of the Phillip type having cross, hexalobe or star-shaped recesses in their heads. In this regard, a distal end 110 of the shank 102 has a tip 112 that is sized and shaped to fit in the cross, hexalobe or star-shaped recesses of the set screws. A perspective view of an illustrative architecture for the tip 112 of shank 102 is provided in FIG. 3. As shown in FIG. 3, the tip 112 has a star-shape in which a plurality of protrusions 300 are provided for engaging recess sidewalls of the set screws. This engagement between the tip 112 and a set screw allows torque to be transferred from the set screw reducer 100 to the set screw.

The tip 112 also comprises a means 302 to frictionally engage a set screw (e.g., set screw 600 of FIGS. 6-7) such that: the set screw remains coupled to the set screw reducer 100 prior to thread engagement between a threaded section (e.g., section 602 of FIGS. 6-7) of the set screw and the object, and during the driving of the set screw into the object; a break-off section (e.g., section 604 of FIGS. 6-7) of the set screw remains coupled to the set screw reducer 100 while being broken apart from the threaded section of the set screw via an application of torque thereto, and while the set screw reducer 100 is being removed away from the object; and the break-off section (e.g., section 604 of FIGS. 6-7) of the set screw can be released from the set screw reducer 100 after the set screw reducer has been moved away from the object. The frictional retention means can include, but is not limited to, a tapered hex shaped tip 112, at least one resiliently biased engagement part (e.g., a ball bearing), and/or a rough surface provided on the tip 112.

The set screw reducer 100 is shown in FIGS. 1-4 as comprising a frictional retention means including resiliently biased engagement parts. In this architecture, the engagement parts comprise ball bearings 304, 308 that are aligned with each other and disposed on opposing sides 402, 404 of the shank's tip 112. The ball bearings 304, 308 are disposed in the shank's tip 112 so that the ball bearings 304, 308 can slide into and out of the shank's tip 112. A resilient member 400 is disposed between the two ball bearings 304, 308. The resilient member 400 is normally in an uncompressed state, and therefore resiliently biases the ball bearings 304, 308 away from each other as shown in FIG. 4. The resilient member 400 can include, but is not limited to, a coil or spring. The ball bearings 304, 308 and resilient member 400 are held in position relative to each other by a cap 306.

When the shank's tip 112 of the set screw reducer 100 is being slid into a socket of a set screw (e.g., set screw 600 of FIGS. 6-7), the ball bearings 304, 308 slide against a sidewall (e.g., sidewall 702 of FIG. 7) of a socket (e.g., socket 700 of FIGS. 6-7) formed in the set screw. This sliding engagement causes the ball bearings 304, 308 to move towards each other and into the shank's tip 112. In effect, the resilient member 400 is compressed by the ball bearings 304, 308. When the ball bearings 304, 308 become aligned with detents (e.g., detents 704, 706 of FIG. 7), a groove or an interior circumferential undercut of the set screw, the resilient member 400 resiliently biases the ball bearings 304, 308 into the detents 704, 706. At this time, a frictional engagement is provided between the set screw reducer 100 and the set screw.

An illustration showing the ball bearings 304, 308 of the set screw reducer 100 disposed in detents 704, 706 of a set screw 600 is provided in FIG. 8. The present solution is not limited to this particular type of frictional means. Other frictional engagement solutions may alternatively or additionally be used as noted above.

As shown in FIGS. 1-4, the set screw reducer 100 also comprises a sleeve 106 slidingly disposed on the shank 102. The sleeve 106 is able to slide in two opposing directions 114, 116 along an elongate length of the shank 102. This sliding ability of the sleeve 106 ensures that the sleeve 106 does not obstruct, prevent and/or interfere with the coupling of the set screw to the set screw reducer 100. In this regard, it should be understood that the sleeve 106 may be slid in direction 116 towards handle 104 prior to when the set screw reducer's operational tip 112 is inserted into the socket/recess of the set screw. In this way, the sleeve 106 is moved to a position (e.g., the position shown in FIG. 9) in which (i) the sleeve does not cover or otherwise block an individual's ability to view tip 112 and/or (ii) a possibility of the sleeve interfering with a coupling between the set screw reducer and the set screw is decreased or eliminated. The sleeve 106 may be maintained in this position while a frictional engagement between the set screw reducer 100 and the set screw is being established.

Notably, the sleeve 106 is provided to prevent or substantially prevent splaying (or spreading outward) of a receiver (e.g., receiver 900 of FIG. 9) while the set screw (e.g., set screw 600 of FIGS. 6-7) is being driven into the same via the set screw reducer 100. Illustrations showing the set screw reducer being used to drive a set screw into a receiver are provided in FIGS. 9-16.

As shown in FIG. 9, a set screw 600 is frictionally coupled to the set screw reducer 100 in the manner described above. As such, the components 100, 600 are simultaneously or concurrently moved in a direction 902 towards the receiver 900 during a set screw driving process as also shown in FIG. 9.

In some scenarios, a sleeve 106 of the set screw reducer 100 may slidingly move in direction 902 towards receiver 900 along the elongate length of the shank 102 while the components 100, 600 are being moved towards the receiver 900. The sliding movement of the sleeve 106 may be caused by a gravitational force being applied thereto. The present solution is not limited in this regard. For example, the sleeve 106 could be held (e.g., manually or via a mechanical means (e.g., a depressible post of the shank)) at a certain location on shank 102 until a later time in the process as discussed below.

Once the set screw 600 is aligned and in contact with a threaded hole 904 of the receiver 900, an individual applies a rotational force to the set screw reducer 100 (e.g., directly via handle 104 or indirectly via use of an external instrument or tool). This rotational force is applied by rotating the set screw reducer 100 in a counter clockwise direction 1000 (not shown) or alternatively in a clockwise direction (shown in FIG. 10). This rotational force or torque is transferred from the set screw reducer 100 to the set screw 600, and causes a threaded portion 602 of the set screw to threadingly engage threads 906 of the receiver 900.

Rotation of the set screw 600 is continued as shown in FIG. 10 so that the set screw 600 abuts a bar, rod or post 1002 that is at least partially inserted through channels formed between sidewalls 1004, 1006 of the receiver 900. Thereafter, the sleeve 106 is slidingly moved in direction 902 towards receiver 900 along the elongate length of the shank 102. The sliding movement of the sleeve 106 may be caused manually by the individual or caused by a gravitational force being applied thereto. The sleeve 106 is slid in direction 902 until either (i) its internal engagement surface 1100 abuts an engagement surface 1102 of the receiver 900 or (ii) stop structures (not shown in FIGS. 9-16) (e.g., one or more protruding structures) of the shank 102 prevent further movement of the sleeve 106 in direction 902. In either case, top portions 1104 of the receiver's sidewalls 1004, 1006 are received in a recess 1106 of the sleeve 106, as shown in FIG. 11. Consequently, the receiver's top portions 1104 are enclosed by a sidewall 1108 of the sleeve 106. Notably, the sleeve sidewall 1108 prevents or substantially prevents the splaying of the receiver's top portions 1104 by the set screw reducer 100 as the set screw is being advanced through the threaded hole 904, as will become apparent with the following discussion.

As shown in FIGS. 12-14, the set screw reducer 100 is continuously rotated so as to advance the set screw 600 through a threaded hole 904 of the receiver 900. During this set screw advancement, the set screw 600 applies a pushing force in direction 902 directly to the bar/rod/post 1002 as it is being advanced through the threaded hole 904. This pushing force causes the bar/rod/post 1002 to travel in direction 902 along with the set screw 600 towards a distal end 1200 of the receiver 900.

Also during the set screw advancement process, the receiver 900 applies a pushing force on the sleeve 106 such that the sleeve slides in direction 1202 along the elongate length of the shank 102. In effect, the receiver's top portions 1104 are continuously disposed in the sleeve 106 while the set screw is being advanced through the threaded hole 904, as shown in FIGS. 12-14. Consequently, the sleeve 106 provides a means to resist the outward splaying of the receiver's top portions 1104 with the set screw reducer 100 throughout the set screw advancement process, and thereby also facilitates an increase speed and efficiency of the set screw advancement process.

As shown in FIG. 14, the set screw 600 is then tightened against the bar/rod/post 1002 to prevent the bar/rod/post from moving relative to the object 1400 (e.g., a screw 1402 with a crown 1404). The set screw 600 exerts a compression or clamping force to the bar/rod/post 1002. In this way, the bar/rod/post 1002 is securely retained in a given position relative to the object 1400 by the set screw 600 and the receiver 900.

Once the set screw 600 is tightened against the bar/rod/post 1002, the set screw reducer 100 is removed from the receiver 900, as shown by FIGS. 15-16. In this regard, a pulling force is applied to the set screw reducer 100 in direction 1500. This pulling force causes the frictional engagement between the set screw reducer 100 and set screw 600 to be discontinued, i.e., the set screw reducer's tip 112 is pulled out of the recess/socket of the set screw 600.

Another tool (not shown) may then be used to apply torque to the set screw so as to (i) cause the break-off section 604 of the set screw to break away from the threaded section 602 of the set screw, and (ii) remove the break-off section 604 of the set screw from the threaded hole 904 of the receiver 900. The present solution is not limited in this regard. Alternatively, the set screw reducer 100 is used instead of the additional tool for performing actions (i) and (ii).

Yet another tool may be used to apply a lateral force to the receiver 900 so as to (i) cause the break-off section 1600 of the receiver to break away from the retainer section 1602 of the receiver, and (ii) move the break-off section 1600 away from the object.

Notably, during some medical procedures, a plurality of set screws may need to be advanced through a plurality of receivers. A plurality of set screw reducers 100 can be concurrently used in such scenarios to advance the set screws through receivers at the same time or in an alternating manner during a single process. For example, a first set screw reducer is used to advance a first set screw by a first amount during a first time period, and a second set screw reducer is used to advance a second set screw by a second amount during a second subsequent time period, where the first and second amounts are the same or different. This process is repeated until the first and second set screws are advanced by a desired amount into one or more objects. The present solution is not limited to the particulars of this example.

Figure 17:
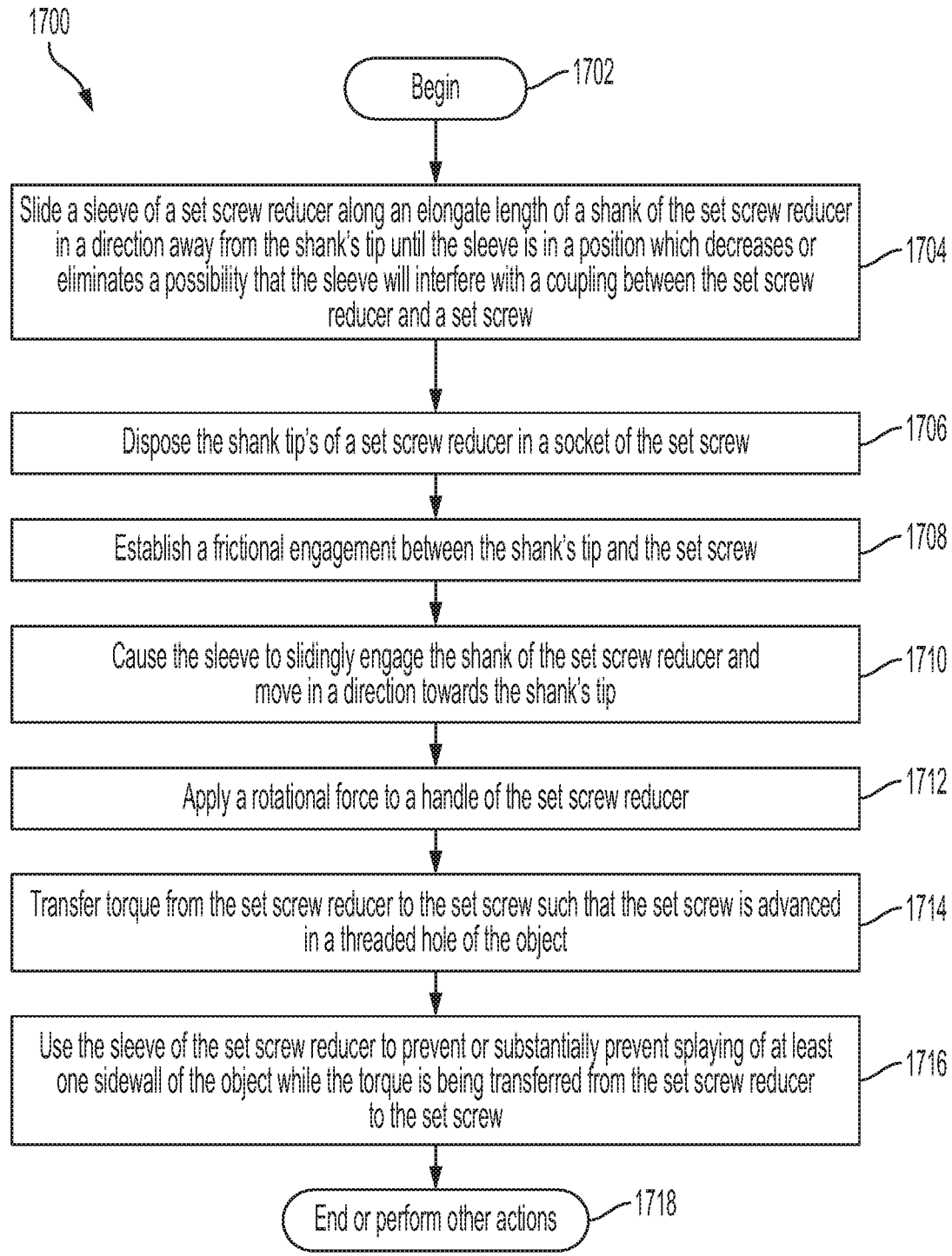
FIG. 17 provides a flow diagram of an illustrative method for advancing a set screw in an object (e.g., during a medical procedure).

Referring now to FIG. 17, there is provided a flow diagram of an illustrative method 1700 for advancing a set screw (e.g., set screw 600 of FIG. 6-7) in an object (e.g., receiver 900 of FIGS. 9-16) (e.g., during a medical procedure). Method 1700 begins with 1702 and continues with 1704 where a sleeve (e.g., sleeve 106 of FIGS. 1-4) of a set screw reducer (e.g., set screw reducer 100 of FIGS. 1-4) is slid along an elongate length of a shank (e.g., shank 102 of FIGS. 1-4) of the set screw reducer in a direction (e.g., direction 116 of FIG. 1) away from the shank's tip (e.g., tip 112 of FIG. 1) until the sleeve is in a positon (e.g., the position shown in FIG. 9) which decreases or eliminates the sleeve's interference with a coupling between the set screw reducer and the set screw. Notably, the sleeve is integrated with the operational parts (e.g., handle 104 and shank 102 of FIGS. 1-4) of the set screw reducer such that the set screw reducer has multiple purposes. These purposes include, but are not limited to, advancing a set screw into an object, removing a set screw from an object, and/or preventing splaying of at least one sidewall of the object while the torque is being transferred from the set screw reducer to the set screw.

Next in 1706, the shank's tip is disposed in a socket (e.g., socket 700 of FIGS. 6-7) of the set screw. A frictional engagement is established in 1708 between the shank's tip and the set screw. In some scenarios, the frictional engagement is established by resiliently biasing at least one engagement part of the set screw reducer into a detent or a groove (e.g., detent or groove 704, 706 of FIG. 7) formed in a sidewall (e.g., sidewall 702 of FIG. 7) of the set screw's socket. The at least one engagement part can include, but is not limited to, a ball bearing (e.g., ball bearing 304, 308 of FIG. 3) that is resiliently biased by a resilient member (e.g., resilient member 400 of FIG. 4) in a direction out and away from the shank tip. The present solution is not limited to the particulars of this scenario.

In 1710, the sleeve is caused to slidingly engage the shank of the set screw reducer and move in a direction (e.g., direction 114 of FIG. 1) towards the shank's tip. A rotational force is then applied in 1712 to the handle of the set screw reducer. The rotational force can be applied with or without the assistance of an external instrument or tool (e.g., wrench 500 of FIG. 5). In this regard, it should be understood that an end (e.g., end 502, 504 of FIG. 5) of the external instrument or tool can be received in a socket (e.g., socket 200 of FIG. 2) formed in the handle of the set screw reducer, and thereafter used to cause rotation of the handle and shank of the set screw reducer.

In 1714, torque is transferred from the set screw reducer to the set screw such that the set screw is advanced in a threaded hole (e.g., threaded hole 904 of FIG. 9) of the object. The torque is transferred from the set screw reducer to the set screw in response to a rotational force being applied to a handle of the set screw reducer.

In 1716, the sleeve of the set screw reducer is used to prevent or substantially prevent splaying of at least one sidewall (e.g., sidewall 1004, 1006 of FIG. 10) of the object while the torque is being transferred from the set screw reducer to the set screw. As part of splaying prevention, the sleeve resists an outward bending of the at least one sidewall of the object throughout the advancement of the set screw in the object. In this regard, it should be understood that: a free end (e.g., end 1104 of FIG. 11) of the at least one sidewall of the object is continuously disposed within a recess (e.g., recess 1106 of FIG. 11) formed in the sleeve, while the set screw reducer is being used to advance the set screw in the object; and the free end of the at least one sidewall of the object causes the sleeve to move along an elongate length of the shank in a direction away from the shank tip while the set screw is being advanced in the object. Subsequently, 1718 is performed where method 1700 ends or other actions are performed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for advancing a set screw in an object, comprising:
   disposing a shank tip of a set screw reducer in a socket of the set screw;
   causing a sleeve integrated with the set screw reducer to slidingly engage a shank of the set screw reducer and move in a direction towards the shank tip;

transferring torque from the set screw reducer to the set screw such that the set screw is advanced in a threaded hole of the object;

using the sleeve of the set screw reducer to substantially prevent splaying of at least one sidewall of the object while the torque is being transferred from the set screw reducer to the set screw; and allowing gravity to cause the sleeve to move in the direction towards the shank tip until the sleeve engages a flange of the shank tip, when the set screw reducer is moved away from the object.

2. The method according to claim 1, further comprising sliding the sleeve along an elongate length of the shank in a direction away from the shank tip until the sleeve is in a position which substantially eliminates sleeve interference with a coupling between the set screw reducer and the set screw.

3. The method according to claim 1, wherein the torque is transferrable from the set screw reducer to the set screw in response to a rotational force being applied to a handle of the set screw reducer.

4. The method according to claim 1, wherein the sleeve, as part of splaying prevention, resists an outward bending of the at least one sidewall of the object throughout the advancement of the set screw in the object.

5. The method according to claim 4, wherein a free end of the at least one sidewall of the object is continuously disposed within a recess formed in the sleeve, while the set screw reducer is being used to advance the set screw in the object.

6. The method according to claim 5, wherein the free end of the at least one sidewall of the object causes the sleeve to move along an elongate length of the shank in a direction away from the shank tip while the set screw is being advanced in the object.

7. The method according to claim 1, further comprising:
receiving an end of an external instrument or tool in a socket formed in a handle of the set screw reducer; and
using the external instrument or tool to cause rotation of the handle.

8. The method according to claim 1, further comprising establishing a frictional engagement between the shank tip and the set screw.

9. The method according to claim 8, wherein the frictional engagement is established by resiliently biasing at least one engagement part of the set screw reducer into a detent or a groove formed in a sidewall of the socket of the set screw.

10. The method according to claim 9, wherein the at least one engagement part comprises a ball bearing that is resiliently biased by a resilient member in a direction out and away from the shank tip.

11. The method according to claim 1, further comprising causing another object to advance concurrently with the set screw within the object when torque is transferred from the set screw reducer to the set screw, the torque causing the set screw to threadingly engage a threaded hole of the object and apply a pushing force on the another object in a direction away from the shank tip.

12. A surgical instrument, comprising:
a shank having a shank tip sized and shaped to fit in a socket of a set screw; and
a sleeve disposed on the shank such that the sleeve slidingly engages the shank and is freely movable at least in a first direction towards the shank tip;
wherein torque is transferable from the shank to the set screw;
wherein the sleeve substantially prevents splaying of at least one sidewall of an object while the torque is being transferred from the shank to the set screw; and
wherein a flange is provided in the shank tip and the sleeve is configured to move in the first direction towards the shank tip until the sleeve engages the flange responsive to a gravitational force.

13. The surgical instrument according to claim 12, wherein the sleeve is slidable along an elongate length of the shank in a direction away from the shank tip until the sleeve is in a position which substantially eliminates the sleeve interference with a coupling between the surgical instrument and the set screw.

14. The surgical instrument according to claim 12, wherein the torque is transferrable from the shank to the set screw in response to a rotational force being applied to a handle of the surgical instrument.

15. The surgical instrument according to claim 12, wherein the sleeve, as part of splaying prevention, resists an outward bending of the at least one sidewall of the object throughout the advancement of the set screw in the object.

16. The surgical instrument according to claim 15, wherein a free end of the at least one sidewall of the object is continuously disposed within a recess formed in the sleeve, while the surgical instrument is being used to advance the set screw in the object.

17. The surgical instrument according to claim 16, wherein the free end of the at least one sidewall of the object causes the sleeve to move along an elongate length of the shank in a direction away from the shank tip while the set screw is being advanced in the object.

18. The surgical instrument according to claim 12, further comprising a handle having a socket to receive an end of an external instrument or tool that facilitates rotation of the handle during advancement of the set screw in the object.

19. The surgical instrument according to claim 12, further comprising a frictional retention structure that establishes a frictional engagement between the shank tip and the set screw.

20. The surgical instrument according to claim 19, wherein the frictional engagement is established by resiliently biasing at least one engagement part of the frictional retention structure into a detent or a groove formed in a sidewall of the socket of the set screw.

21. The surgical instrument according to claim 20, wherein the at least one engagement part comprises a ball bearing that is resiliently biased by a resilient member in a direction out and away from the shank tip.

* * * * *